(12) United States Patent
Lostetter (10) Patent No.: US 11,395,750 B2
(45) Date of Patent: Jul. 26, 2022

(54) STENT GRAFTS AND METHODS OF USE FOR TREATING ANEURYSMS

(71) Applicant: Bolton Medical, Inc., Sunrise, FL (US)

(72) Inventor: Timothy Lostetter, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 0 days.

(21) Appl. No.: 16/507,314

(22) Filed: Jul. 10, 2019

(65) Prior Publication Data

US 2019/0328557 A1 Oct. 31, 2019

Related U.S. Application Data

(62) Division of application No. 15/604,032, filed on May 24, 2017, now abandoned.

(Continued)

(51) Int. Cl.
*A61F 2/856* (2013.01)
*A61F 2/07* (2013.01)
(Continued)

(52) U.S. Cl.
CPC ............... *A61F 2/856* (2013.01); *A61F 2/07* (2013.01); *A61F 2/89* (2013.01); *A61F 2/852* (2013.01); *A61F 2002/061* (2013.01); *A61F 2002/065* (2013.01); *A61F 2002/067* (2013.01); *A61F 2002/8486* (2013.01); *A61F 2220/005* (2013.01); *A61F 2220/0008* (2013.01); *A61F 2250/0039* (2013.01)

(58) Field of Classification Search
USPC .................................................. 623/1.1–3.1
See application file for complete search history.

(56) References Cited

U.S. PATENT DOCUMENTS

| 4,501,263 A | 2/1985 | Harbuck |
| 5,123,917 A | 6/1992 | Lee |

(Continued)

FOREIGN PATENT DOCUMENTS

| CN | 201230914 Y | 5/2009 |
| CN | 101601618 A | 12/2009 |

(Continued)

OTHER PUBLICATIONS

International Preliminary Report on Patentability for International Application No. PCT/US2017/034223 dated Nov. 27, 2018.

(Continued)

*Primary Examiner* — Yashita Sharma
(74) *Attorney, Agent, or Firm* — Foley Hoag LLP (57) ABSTRACT

A stent graft includes a tubular aortic component that defines a lumen and a fenestration with a pocket at the fenestration. At least one proximal tunnel graft extends proximally within the lumen from the proximal opening of the pocket and is secured at a proximal end to the tubular component, and at least one distal tunnel graft extends distally within the lumen from the distal opening of the pocket and is secured at a distal end to the tubular aortic component. The stent graft can further include at least one branch stent graft, each of which extends through the fenestration and within at least one of the proximal tunnel graft or the distal tunnel graft. The stent graft can be implanted in a patient to thereby treat an aneurysm, such as a suprarenal or thoracoabdominal aortic aneurysm.

19 Claims, 8 Drawing Sheets

Related U.S. Application Data (60) Provisional application No. 62/341,234, filed on May 25, 2016.

(51) Int. Cl.

| | | |
|---|---|---|
| *A61F 2/89* | (2013.01) | |
| *A61F 2/852* | (2013.01) | |
| *A61F 2/06* | (2013.01) | |
| *A61F 2/848* | (2013.01) | |

(56) References Cited

U.S. PATENT DOCUMENTS

| | | |
|---|---|---|
| 5,231,989 A | 8/1993 | Middleman |
| 5,507,769 A | 4/1996 | Marin et al. |
| 5,575,817 A | 11/1996 | Martin |
| 5,683,449 A | 11/1997 | Marcade |
| 5,755,772 A | 5/1998 | Evans et al. |
| 5,843,160 A | 12/1998 | Rhodes |
| 5,855,598 A | 1/1999 | Pinchuk |
| 5,984,955 A | 11/1999 | Wisselink |
| 6,059,824 A | 5/2000 | Taheri |
| 6,171,334 B1 | 1/2001 | Cox |
| 6,187,033 B1 | 2/2001 | Schmitt et al. |
| 6,210,429 B1 | 4/2001 | Vardi et al. |
| 6,280,464 B1 | 8/2001 | Hayashi |
| 6,306,141 B1 | 10/2001 | Jervis |
| 6,344,056 B1 | 2/2002 | Dehdashtian |
| 6,395,018 B1 | 5/2002 | Castaneda |
| 6,428,565 B1 | 8/2002 | Wisselink |
| 6,585,756 B1 | 7/2003 | Strecker |
| 6,592,615 B1 | 7/2003 | Marcade |
| 6,595,963 B1 | 7/2003 | Barbut |
| 6,645,242 B1 | 11/2003 | Quinn |
| 6,676,699 B2 | 1/2004 | Shiu |
| 6,814,752 B1 | 11/2004 | Chuter |
| 7,144,421 B2 | 12/2006 | Carpenter |
| 7,294,147 B2 | 11/2007 | Hartley |
| 7,407,509 B2 | 8/2008 | Greenberg |
| 7,435,253 B1 | 10/2008 | Hartley et al. |
| 7,438,721 B2 | 10/2008 | Doig et al. |
| 7,537,606 B2 | 5/2009 | Hartley |
| 7,550,004 B2 | 6/2009 | Bahler |
| 7,641,646 B2 | 1/2010 | Mafi |
| 7,731,744 B1 | 6/2010 | Cox |
| 7,763,063 B2 | 7/2010 | Arbefeuille et al. |
| 7,828,837 B2 | 11/2010 | Khoury |
| 7,854,758 B2 | 12/2010 | Taheri |
| 7,914,572 B2 | 3/2011 | Hartley |
| 8,007,605 B2 | 8/2011 | Arbefeuille |
| 8,021,419 B2 | 9/2011 | Hartley |
| 8,048,140 B2 | 11/2011 | Purdy |
| 8,052,736 B2 | 11/2011 | Doig et al. |
| 8,062,345 B2 | 11/2011 | Ouellette et al. |
| 8,062,349 B2 | 11/2011 | Moore et al. |
| 8,070,790 B2 | 12/2011 | Berra et al. |
| 8,092,511 B2 | 1/2012 | Chuter |
| 8,105,372 B1 | 1/2012 | Chuter |
| 8,167,930 B2 | 5/2012 | Allen et al. |
| 8,172,895 B2 | 5/2012 | Anderson |
| 8,267,988 B2 | 9/2012 | Hamer |
| 8,273,115 B2 | 9/2012 | Hamer |
| 8,292,943 B2 | 10/2012 | Berra et al. |
| 8,308,790 B2 | 11/2012 | Arbefeuille et al. |
| 8,333,800 B2 | 12/2012 | Bruszewski |
| 8,337,546 B2 | 12/2012 | Bruszewski |
| 8,361,134 B2 | 1/2013 | Hartley |
| 8,394,136 B2 | 3/2013 | Hartley |
| 8,449,595 B2 | 5/2013 | Ouellette et al. |
| 8,474,120 B2 | 7/2013 | Hagaman |
| 8,500,792 B2 | 8/2013 | Berra |
| 8,523,934 B2 | 9/2013 | Purdy |
| 8,545,549 B2 | 10/2013 | Hartley |
| 8,556,961 B2 | 10/2013 | Quinn |
| 8,574,284 B2 | 11/2013 | Roeder |
| 8,574,288 B2 | 11/2013 | Hartley |
| 8,636,788 B2 | 1/2014 | Arbefeuille et al. |
| 8,663,310 B2 | 3/2014 | Greenberg |
| 8,672,993 B2 | 3/2014 | Chuter et al. |
| 8,728,145 B2 | 5/2014 | Chuter |
| 8,740,963 B2 | 6/2014 | Arbefeuille et al. |
| 8,740,966 B2 | 6/2014 | Brocker |
| 8,753,386 B2 | 6/2014 | Shaw |
| 8,795,349 B2 | 8/2014 | Huser |
| 8,808,358 B2 | 8/2014 | Khoury |
| 8,870,939 B2 | 10/2014 | Roeder |
| 8,870,946 B1 | 10/2014 | Quinn |
| 8,940,040 B2 | 1/2015 | Shahriari |
| 8,945,202 B2 | 2/2015 | Mayberry et al. |
| 8,945,205 B2 | 2/2015 | Greenberg |
| 8,992,593 B2 | 3/2015 | Chuter et al. |
| 8,998,970 B2 | 4/2015 | Arbefeuille et al. |
| 8,998,971 B1 | 4/2015 | Kelly |
| 9,034,027 B2 | 5/2015 | Ivancev |
| 9,095,456 B2 | 8/2015 | Ivancev et al. |
| 9,101,455 B2 | 8/2015 | Roeder et al. |
| 9,101,506 B2 | 8/2015 | Arbefeuille et al. |
| 9,149,382 B2 | 10/2015 | Greenberg et al. |
| 9,173,755 B2 | 11/2015 | Berra et al. |
| 9,198,786 B2 | 12/2015 | Moore et al. |
| 9,220,617 B2 | 12/2015 | Berra |
| 9,259,336 B2 | 2/2016 | Schaeffer et al. |
| 9,320,631 B2 | 4/2016 | Moore et al. |
| 9,333,104 B2 | 5/2016 | Ouellette et al. |
| 9,345,595 B2 | 5/2016 | Brocker et al. |
| 9,364,314 B2 | 6/2016 | Berra et al. |
| 9,408,734 B2 | 8/2016 | Arbefeuille et al. |
| 9,408,735 B2 | 8/2016 | Arbefeuille et al. |
| 9,439,751 B2 | 9/2016 | White et al. |
| 9,463,102 B2 | 10/2016 | Kelly |
| 9,554,929 B2 | 1/2017 | Arbefeuille et al. |
| 9,561,124 B2 | 2/2017 | Arbefeuille et al. |
| 9,592,112 B2 | 3/2017 | Arbefeuille et al. |
| 9,597,209 B2 | 3/2017 | Khoury |
| 9,649,188 B2 | 5/2017 | Hartley |
| 9,655,712 B2 | 5/2017 | Berra et al. |
| 9,724,187 B2 | 8/2017 | Ivancev et al. |
| 9,827,123 B2 | 11/2017 | Arbefeuille et al. |
| 9,855,130 B2 | 1/2018 | Roeder et al. |
| 9,861,505 B2 | 1/2018 | Khoury |
| 9,877,857 B2 | 1/2018 | Arbefeuille et al. |
| 9,907,686 B2 | 3/2018 | Ouellette et al. |
| 9,913,743 B2 | 3/2018 | Arbefeuille et al. |
| 9,925,080 B2 | 3/2018 | Arbefeuille et al. |
| 10,105,248 B2 | 10/2018 | Berra et al. |
| 10,105,250 B2 | 10/2018 | Berra |
| 10,182,930 B2 | 1/2019 | Moore et al. |
| 10,213,291 B2 | 2/2019 | Berra et al. |
| 10,299,951 B2 | 5/2019 | Arbefeuille et al. |
| 10,307,275 B2 | 6/2019 | Berra et al. |
| 10,390,932 B2 | 8/2019 | Lostetter |
| 11,065,100 B2 | 7/2021 | Parodi et al. |
| 2002/0013620 A1 | 1/2002 | Kujawski |
| 2002/0052643 A1 | 5/2002 | Wholey et al. |
| 2002/0062133 A1 | 5/2002 | Gilson et al. |
| 2003/0120333 A1 | 6/2003 | Ouriel et al. |
| 2003/0130725 A1 | 7/2003 | DePalma et al. |
| 2003/0199967 A1 | 10/2003 | Hartley et al. |
| 2003/0204242 A1 | 10/2003 | Zarins |
| 2004/0006299 A1 | 1/2004 | Barbut |
| 2004/0215327 A1 | 10/2004 | Doig et al. |
| 2005/0010277 A1 | 1/2005 | Chuter |
| 2005/0059923 A1 | 3/2005 | Gamboa |
| 2005/0102018 A1 | 5/2005 | Carpenter |
| 2005/0131518 A1 | 6/2005 | Hartley et al. |
| 2005/0131523 A1 | 6/2005 | Bashir et al. |
| 2005/0177222 A1 | 8/2005 | Mead |
| 2006/0095118 A1 | 5/2006 | Hartley |
| 2006/0184228 A1 | 8/2006 | Khoury |
| 2006/0229707 A1 | 10/2006 | Khoury |
| 2007/0055350 A1 | 3/2007 | Erickson et al. |
| 2007/0106368 A1 | 5/2007 | Vonderwalde |
| 2007/0135818 A1 | 6/2007 | Moore et al. |
| 2007/0168013 A1 | 7/2007 | Douglas |

(56) References Cited

U.S. PATENT DOCUMENTS

| | | |
|---|---|---|
| 2007/0198078 A1 | 8/2007 | Berra et al. |
| 2007/0203566 A1 | 8/2007 | Arbefeuille et al. |
| 2008/0077226 A1 | 3/2008 | Ouellette et al. |
| 2008/0091260 A1 | 4/2008 | Pomeranz et al. |
| 2008/0109066 A1 | 5/2008 | Quinn |
| 2008/0114444 A1 | 5/2008 | Yu |
| 2008/0147163 A1 | 6/2008 | Allen |
| 2008/0264102 A1 | 10/2008 | Berra |
| 2008/0281399 A1 | 11/2008 | Hartley et al. |
| 2009/0012597 A1 | 1/2009 | Doig et al. |
| 2009/0048663 A1 | 2/2009 | Greenberg |
| 2009/0125100 A1 | 5/2009 | Mead |
| 2009/0264988 A1 | 10/2009 | Mafi |
| 2009/0306763 A1 | 12/2009 | Roeder |
| 2009/0319022 A1 | 12/2009 | Hartley |
| 2010/0030255 A1 | 2/2010 | Berra et al. |
| 2010/0049298 A1 | 2/2010 | Hamer et al. |
| 2010/0057186 A1 | 3/2010 | West |
| 2010/0234932 A1 | 9/2010 | Arbefeuille |
| 2011/0087318 A1 | 4/2011 | Daugherty et al. |
| 2011/0118821 A1 | 5/2011 | Brocker et al. |
| 2011/0172762 A1 | 7/2011 | Hartley |
| 2011/0208288 A1 | 8/2011 | Arbefeuille et al. |
| 2011/0218607 A1 | 9/2011 | Arbefeuille et al. |
| 2011/0245906 A1 | 10/2011 | DiMatteo et al. |
| 2011/0257731 A1 | 10/2011 | Hartley |
| 2011/0313503 A1 | 12/2011 | Berra et al. |
| 2012/0046728 A1 | 2/2012 | Huser et al. |
| 2012/0123464 A1 | 5/2012 | Rasmussen |
| 2012/0130472 A1 | 5/2012 | Shaw |
| 2012/0158121 A1 | 6/2012 | Ivancev et al. |
| 2012/0245672 A1 | 9/2012 | Arbefeuille et al. |
| 2012/0271401 A1 | 10/2012 | Bruszewski |
| 2012/0296414 A1 | 11/2012 | Hartley |
| 2012/0310324 A1 | 12/2012 | Benary et al. |
| 2013/0013053 A1 | 1/2013 | Hartley |
| 2013/0079870 A1 | 3/2013 | Roeder et al. |
| 2013/0138199 A1 | 5/2013 | Ivancev et al. |
| 2013/0184806 A1 | 7/2013 | Arbefeuille |
| 2013/0197627 A1 | 8/2013 | Jensen |
| 2013/0211506 A1 | 8/2013 | Dake et al. |
| 2013/0268059 A1 | 10/2013 | Hagaman |
| 2013/0282103 A1 | 10/2013 | Madjarov et al. |
| 2014/0039597 A9 | 2/2014 | Arbefeuille et al. |
| 2014/0046428 A1 | 2/2014 | Cragg et al. |
| 2014/0135890 A9 | 5/2014 | Berra |
| 2014/0135892 A1 | 5/2014 | Arbefeuille et al. |
| 2014/0135896 A1 | 5/2014 | Arbefeuille et al. |
| 2014/0148890 A9 | 5/2014 | Ouellette et al. |
| 2014/0243952 A1 | 8/2014 | Parodi |
| 2014/0277340 A1 | 9/2014 | White et al. |
| 2014/0277347 A1 | 9/2014 | Daugherty et al. |
| 2014/0277370 A1 | 9/2014 | Brocker |
| 2014/0277379 A1 | 9/2014 | Vogel et al. |
| 2014/0288627 A1 | 9/2014 | Ouellette et al. |
| 2015/0173922 A1 | 6/2015 | Arbefeuille et al. |
| 2015/0202066 A1 | 7/2015 | Berra et al. |
| 2015/0202068 A1 | 7/2015 | Arbefeuille et al. |
| 2015/0209164 A1 | 7/2015 | Kelly |
| 2015/0272755 A1 | 10/2015 | Arbefeuille et al. |
| 2016/0045350 A1 | 2/2016 | Berra et al. |
| 2016/0081787 A1 | 3/2016 | Parodi |
| 2016/0184077 A1 | 6/2016 | Choubey et al. |
| 2016/0184078 A1 | 6/2016 | Choubey et al. |
| 2016/0184115 A1 | 6/2016 | Ondersma et al. |
| 2016/0270901 A1 | 9/2016 | Berra |
| 2016/0270936 A1 | 9/2016 | Berra |
| 2016/0310301 A1 | 10/2016 | Moore |
| 2016/0338867 A1 | 11/2016 | White |
| 2017/0000600 A1 | 1/2017 | Berra |
| 2017/0007392 A1 | 1/2017 | Lourenco et al. |
| 2017/0100232 A1 | 4/2017 | Arbefeuille |
| 2017/0100271 A1 | 4/2017 | Arbefeuille |
| 2017/0135807 A1 | 5/2017 | Arbefeuille |
| 2017/0151076 A9 | 6/2017 | Arbefeuille |
| 2017/0165090 A1 | 6/2017 | Arbefeuille |
| 2017/0165091 A1 | 6/2017 | Arbefeuille |
| 2017/0281332 A1 | 10/2017 | Lostetter |
| 2017/0281382 A1 | 10/2017 | Lostetter |
| 2017/0319359 A1 | 11/2017 | Mehta |
| 2017/0325977 A1 | 11/2017 | Sarac et al. |
| 2017/0340433 A1 | 11/2017 | Berra |
| 2017/0340462 A1 | 11/2017 | Lostetter |
| 2018/0071123 A1 | 3/2018 | Arbefeuille |
| 2018/0078394 A1 | 3/2018 | Zimmerman et al. |
| 2018/0110638 A1 | 4/2018 | Berra et al. |
| 2018/0140448 A1 | 5/2018 | Arbefeuille et al. |
| 2018/0206972 A1 | 7/2018 | Arbefeuille et al. |
| 2019/0192324 A1 | 6/2019 | Arbefeuille et al. |

FOREIGN PATENT DOCUMENTS

| | | |
|---|---|---|
| CN | 102379757 A | 3/2012 |
| CN | 102488575 A | 6/2012 |
| CN | 102641164 A | 8/2012 |
| CN | 103876860 A | 6/2014 |
| CN | 203841852 U | 9/2014 |
| CN | 104287871 A | 1/2015 |
| CN | 102 973 303 B | 2/2015 |
| CN | 104367400 A | 2/2015 |
| CN | 104546221 A | 4/2015 |
| CN | 105030373 A | 11/2015 |
| CN | 105213076 A | 1/2016 |
| EP | 1487380 B1 | 2/2008 |
| EP | 2051663 B1 | 11/2009 |
| EP | 2139429 B1 | 6/2011 |
| EP | 1765222 B1 | 10/2012 |
| EP | 2410945 B1 | 11/2012 |
| EP | 1983933 B1 | 1/2013 |
| EP | 2182889 B1 | 9/2014 |
| EP | 2331013 B1 | 11/2014 |
| EP | 2420206 B1 | 1/2015 |
| EP | 2450006 B1 | 1/2015 |
| WO | WO 2001/032103 A1 | 5/2001 |
| WO | WO 2002/038085 A1 | 5/2002 |
| WO | WO 2003/082153 A2 | 10/2003 |
| WO | WO 2005/023149 A2 | 3/2005 |
| WO | WO 2006/034276 A1 | 3/2006 |
| WO | WO 2006/113501 A1 | 10/2006 |
| WO | WO 2007/092276 A2 | 8/2007 |
| WO | WO 2007/123956 A2 | 11/2007 |
| WO | WO 2008/021557 A1 | 2/2008 |
| WO | WO 2009/020653 A1 | 2/2009 |
| WO | WO 2009/124124 A1 | 10/2009 |
| WO | WO 2010/005524 A2 | 1/2010 |
| WO | WO 2010/024879 A1 | 3/2010 |
| WO | WO 2010/105195 A2 | 9/2010 |
| WO | WO 2011/056638 A1 | 5/2011 |
| WO | WO-2012/051532 A2 | 4/2012 |
| WO | WO 2013/025727 A1 | 2/2013 |
| WO | WO 2013/071222 A1 | 5/2013 |
| WO | WO 2013/074990 A1 | 5/2013 |
| WO | WO 2013/154749 A1 | 10/2013 |
| WO | WO 2014/149022 A1 | 9/2014 |
| WO | WO 2014/172501 A2 | 10/2014 |
| WO | WO 2015/116715 A1 | 8/2015 |
| WO | WO-2015/188775 A1 | 12/2015 |
| WO | WO 2016/049037 A1 | 3/2016 |
| WO | WO 2017218474 | 12/2017 |
| WO | WO 2018/031632 A1 | 2/2018 |
| WO | WO 2018026768 | 2/2018 |

OTHER PUBLICATIONS

Notification of Transmittal of the International Search Report and The Written Opinion or the International Searching Authority, or the Declaration for International Application No. PCT/US2017/034223, entitled, "Stent Grafts and Methods of Use for Treating Aneurysms," dated Aug. 22, 2017.

"Bolton Medical Thoracic Branch Graft Case Presentation," Charing Cross Symposium Annual Meeting, London, Apr. 8-12, 2011.

(56) References Cited

OTHER PUBLICATIONS

Browne, T.F., et al., "Endovascular and Surgical Techniques: A Fenestrated Covered Suprarenal Aortic Stent," Eur J Vasc Endovasc Surg, 18:445-449 (1999).

Chuter, T.A.M., et al., "Development of a Branched Stent-Graft for Endovascular Repair of Aortic Arch Aneurysms," J Endovasc Ther, 10:940-945 (2003).

Chuter, T.A.M., et al., "Modular Branched Stent Graft for Endovascular Repair of Aortic Arch Aneurysm and Dissection," J Vasc Surg, 38:859-863 (2003).

Funovics, M., "Branched Endografts for Aortic Arch Aneurysms—How Close Are We?," CIRSE 2011 Conference, Munich, Germany, Session No. 802.3 (Sep. 10-14, 2011).

Funovics, M., "TEVAR in the Ascending Aorta: A New Frontier for Endografting—Preliminary Results and Technology Transfer," Focus Meeting, Bolton Medical Inc., Barcelona, Spain (Oct. 2011).

Inoue, K., et al., "Aortic Arch Reconstruction by Transluminally Placed Endovascular Branched Stent Graft," Circulation, 100(Suppl II):II-316-II-321 (1999).

Inoue, K., et al., "Clinical Endovascular Placement of Branched Graft for Type B Aortic Dissection," J Thorac Cardiovasc Surg, 112:1111-1113 (1996).

Inoue, K., et al., "Transluminal Endovascular Branched Graft Placement for a Pseudoaneurysm: Reconstruction of the Descending Thoracic Aorta Including the Celiac Axis," J Thorac Cardiovasc Surg, 114:859-861 (1997).

Kinney, E.V., et al., "Repair of Mycotic Paravisceral Aneurysm with a Fenestrated Stent-Graft," J Endovasc Ther,7:192-197 (2000).

Lioupis, C., et al., "Treatment of Aortic Arch Aneurysms with a Modular Transfemoral Multibranched Stent Graft: Initial Experience," European Journal of Vascular and Endovascular Surgery, 43:525-532 (2012).

Martinelli, L., "Partial Ascending Aorta and Total Arch Reconstruction with Bolton Medical Branched Thoracic Endograft," Cardiovasular Surgery Meeting, Bologna, Italy (Nov. 14-15, 2011).

Oderich, G.S., et al., "Initial Experience with the Gore Excluder Thoracoabdominal Branch Endoprosthesis," Supplement to Endovascular Today, 15(3):12-16 (2016).

Ouriel, K. and Clair, D.G., "Branched Device to Preserve Hypogastric Arterial Flow with Thoracoabdominal Aneurysm Repair," J Vasc Surg, 37:481 (2003).

Simring, D., et al., "Total Endovascular Repair of the Arch: Branched Endografting Makes it Easy," *Tecnicas Endovasculares*, 14(1):3712-3716 (2011).

Wisselink, W., et al., "Endoluminal Repair of Aneurysms Containing Ostia of Essential Branch Arteries: An Experimental Model," J Endovasc Surg, 6:171-179 (1999).

Non-Final Office Action dated Feb. 11, 2019, U.S. Appl. No. 15/604,032.

STENT GRAFTS AND METHODS OF USE FOR TREATING ANEURYSMS

RELATED APPLICATION

This application is a divisional of U.S. application Ser. No. 15/604,032, filed May 24, 2017 which claims the benefit of U.S. Provisional Application No. 62/341,234 filed on May 25, 2016. The entire teachings of the above applications are incorporated herein by reference.

BACKGROUND

Suprarenal abdominal aortic aneurysms (AAA) and thoracoabdominal aortic aneurysms (TAAA) are life-threatening conditions that represent surgical challenges. Although open surgical repair of these aneurysms can treat the diseased area of the aorta, there are considerable risks with open repair, primarily as a consequence of ischemic insult to the spinal cord, kidneys and surrounding abdominal viscera resulting from surgery. Currently, open surgical techniques to repair suprarenal AAA and TAAA include distal aortic perfusion via extracorporeal circuits, in-line shunts, and cold renal perfusion to reduce the potential of ischemic injury to the spinal cord and renovisceral areas.

Therefore, a need exits for new and improved endovascular repair devices and methods to treat suprarenal AAA and TAAA that minimize trauma to the patient, and loss of blood flow to the spinal cord and surrounding viscera.

SUMMARY OF THE INVENTION

The present invention relates to stent grafts and methods of using stent grafts to treat aortic vascular damage, such as vascular damage associated with suprarenal AAA and TAAA, including aneurysms, penetrating ulcers and dissection.

In an embodiment, the invention is a stent graft comprising: a tubular aortic component defining a lumen having a proximal end, a distal end, a major longitudinal axis, and defining a fenestration between the proximal end and the distal end; a pocket at the fenestration, the pocket defining a pocket proximal opening and a pocket distal opening opposite the pocket proximal opening within the lumen; at least one proximal tunnel graft having a proximal tunnel graft proximal end, and at least one proximal tunnel graft distal end, and defining a proximal tunnel graft lumen, the proximal tunnel graft extending proximally within the lumen from the pocket proximal opening and being secured at its proximal end to the tubular aortic component; and at least one distal tunnel graft having a distal tunnel graft proximal end and a distal tunnel graft distal end, and defining at least one distal tunnel graft lumen, the distal tunnel graft extending distally within the lumen from the distal opening of the pocket and being secured at its distal end to the tubular aortic component.

In another embodiment, the invention is a method for treating a suprarenal or a thoracoabdominal aortic aneurysm. A stent graft is delivered through an aorta to an aneurysm site of a patient, the stent graft being radially and releasably constrained by a distal end of a control catheter of a delivery device. The stent graft includes: a tubular aortic component defining a lumen having a proximal end, a distal end, a major longitudinal axis, and defining a fenestration between the proximal end and the distal end; a pocket at the fenestration, the pocket defining a proximal opening and a distal opening opposite the proximal opening within the lumen; at least one proximal tunnel graft having a proximal tunnel graft proximal end and a proximal tunnel graft distal end, and defining at least one proximal tunnel graft lumen, the proximal tunnel graft extending proximally within the lumen from the proximal opening of the pocket and being secured at its proximal end to the tubular aortic component; and at least one distal tunnel graft having a distal tunnel graft proximal end and a distal tunnel graft distal end, and defining at least one distal tunnel graft lumen, the distal tunnel graft extending distally within the lumen from the distal opening of the pocket and being secured at its distal end to the tubular aortic component. The fenestration is aligned at the aneurysm site of the patient with at least one branch of the aorta at the aneurysm site. The tubular aortic component (stent graft) is released from the delivery device, such as by retracting a control catheter of the delivery device. Each of at least one branch stent graft is delivered through the distal end and the proximal end of the stent graft and through the distal tunnel graft or the proximal tunnel graft to the fenestration, and through the fenestration to a branch of the aorta at the aneurysm site of the patient, whereby the branch stent graft is secured into the distal tunnel graft lumen or the proximal tunnel graft lumen while being radially constrained at the opposite end of the branch stent graft by a branch delivery device. Each branch stent graft is released from the branch delivery device to thereby complete implantation of the branch stent graft and treat the suprarenal or thoracoabdominal aortic aneurysm.

The stent grafts and methods of the invention have several advantages, including, for example, defining a fenestration that reduces the profile of the stent graft which, in turn, has the advantage of accommodating branch stent grafts within tunnel grafts to minimize the diameter of a prosthesis placed in a diseased aorta. The length and diameter of the fenestration can be customized for individual patients depending upon the degree and extent of the suprarenal AAA and TAAA to permit the surgeon to minimize trauma in the area of the diseased aorta while providing the surgeon with a decreased profile for introducing branch stent grafts to branch vessels of organs and tissues in the area of the diseased aorta.

The stent grafts and methods of the invention also have the advantage of providing greater flexibility of choice to the surgeon introducing branch stent grafts, arranging them in either an antegrade or retrograde configuration, to accommodate the anatomical features specific to tissue surrounding the aneurysm. In the case of arteries, antegrade is the flow of blood away from the heart and in the case of veins antegrade is the flow of blood towards the heart. In the case of arteries, retrograde is the flow of blood towards the heart and in the case of veins retrograde is the flood of blood away from the heart. For example, antegrade placement of a branch stent graft in an aorta refers to the implantation of a branch stent graft that results in a portion of the branch stent graft extending from the fenestration in the tubular aortic component (stent graft with fenestration implanted in the aorta at the site of an aneurysm) in the same direction as the flow of blood. In contrast, retrograde placement of a branch stent graft in an aorta refers to the implantation of a branch stent graft that results in a portion of the branch stent graft extending from the fenestration in the aortic stent graft component in a direction that is opposite the flow of blood from the heart.

Further, the proximal and distal tunnel grafts are each secured to the aortic graft component at their proximal and distal ends, respectively. As a result, implantation of branch stent grafts which, in abdominal aortic aneurysms or thoracoabdominal aortic aneurysm surgeries, must be through either the proximal or distal end of the aortic stent graft component, is facilitated by relatively stable positioning of the proximal end of the proximal tunnel graft and the distal end of the distal tunnel graft within the aortic stent graft component.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The same number in different drawings represents the same item. The drawings are not necessarily to scale, emphasis instead being placed upon illustrating embodiments of the present invention.

DETAILED DESCRIPTION OF THE INVENTION

The invention is generally directed to prostheses for use in treating vascular disease, such as implantation of the prostheses at a site of an aortic aneurysm.

The features and other details of the invention, either as steps of the invention or as combinations of parts of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

A description of example embodiments of the invention follows.

When reference is made herein to a prosthesis to be delivered, or implanted in a patient, such as a vascular repair device, the word "proximal" means that portion of the prosthesis or component of the prosthesis that is relatively close to the heart of the patient and "distal" means that portion of the prosthesis or component of the prosthesis that is relatively far from the heart of the patient.

When, however, reference is made to a delivery system or a component of a delivery system employed to deliver, or implant a vascular repair device, the word, "proximal," as employed herein, means closer to the clinician using the delivery system. "Distal," as that term is employed herein, means, when reference is made to a delivery system or a component of a delivery system, further away from the clinician using the delivery system.

For clarity, the word "proximate" means "close to," as opposed to the meanings ascribed to "proximal" or "distal" above with respect to either the vascular repair device or delivery system.

Figure 1:
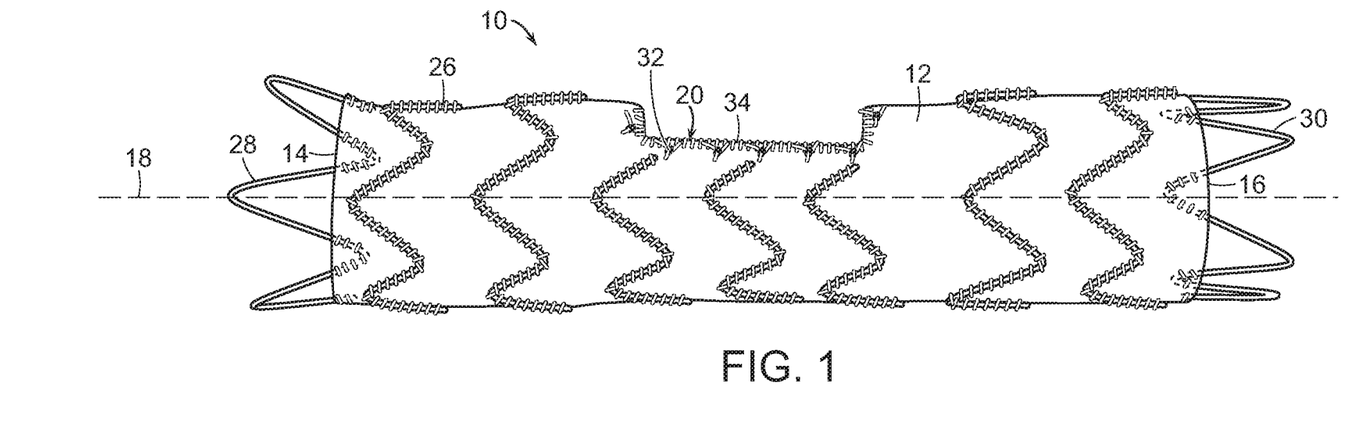
FIG. 1 is a side view of one embodiment of a stent graft of the invention.

One embodiment of the stent graft of the invention is shown in FIG. 1. As shown therein, stent graft (10) includes tubular aortic component (12) defining a lumen having proximal end (14), distal end (16), major longitudinal axis (18), and defining fenestration (20) between proximal end (14) and distal end (16) of stent graft (10). Tubular aortic component (12) is made from suitable materials, such as are known to those skilled in the art, including, for example, expanded polytetrafluoroethylene (PTFE), such as expanded PTFE (ePTFE), and polyethylene terephthalate (PET), such as woven polyester. Fenestration (20) defines fenestration proximal end (22) and fenestration distal end (24). Stents (26) extend about at least a portion of the circumference of tubular aortic component (12) between proximal end (14) and distal end (16). Proximal bare stent (28) and distal bare stent (30) are secured to proximal end (14) and distal end (16), respectively. Stents (26) and bare stents (28, 30) are sutured to tubular aortic component (12) by suitable means known to those skilled in the art, such as by sutures (31), including sutures fabricated of polyester ePTFE (expanded polytetrafluoroethylene), polyglycolic acid, polylactic acid, monocryl and polydioxanone, non-absorbable nylon, polyester, PVDF (polyvinylidene difluoride) and polypropylene. Stents (26) and bare stents (28, 30) are formed of a suitable material, such as is known to those skilled in the art, including nitinol. Suitable radiographic markers (32), such as are known to those skilled in the art, are sutured to periphery (34) of fenestration (20).

Figure 2A:
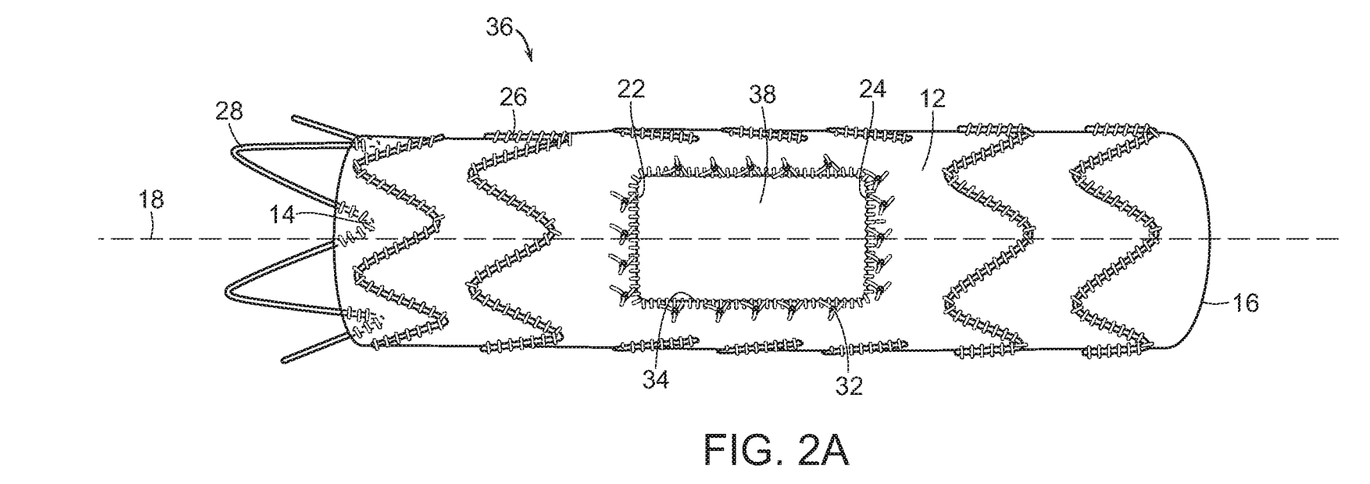
FIG. 2A is a side view of another embodiment of a stent graft of the invention, like that of FIG. 1 but lacking a distal bare stent and rotated 90° about a major longitudinal axis.
Figures 2B, 3A:
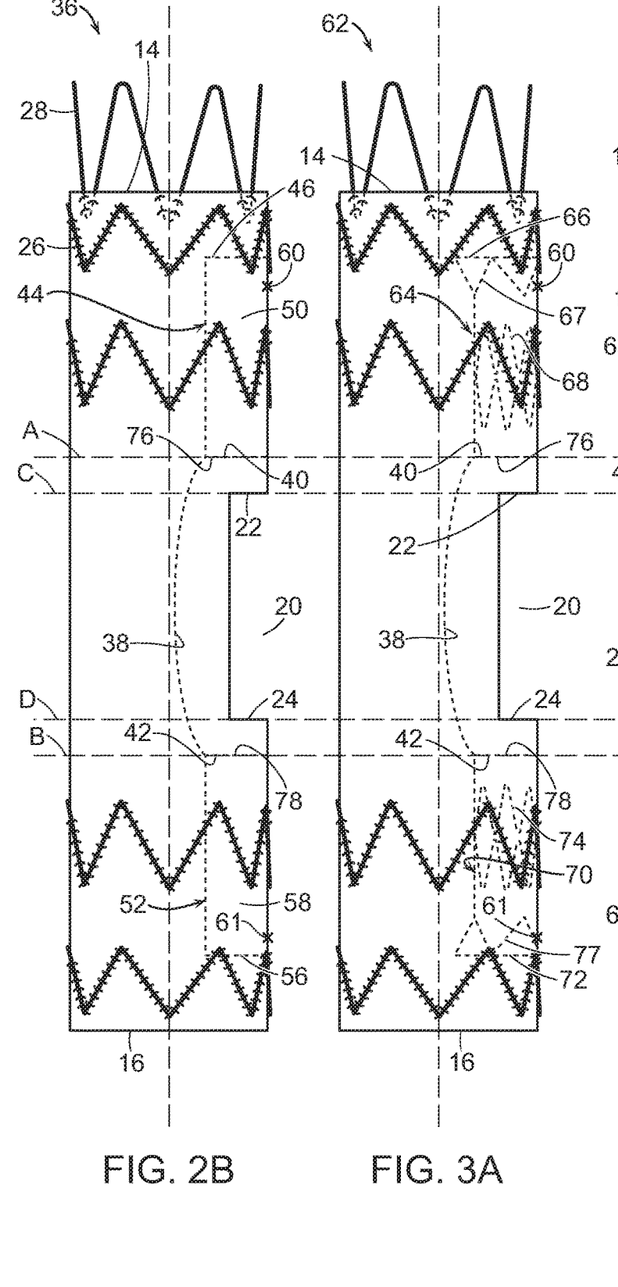
FIG. 2B is a side view of the embodiment of FIG. 2A showing, in dashed-lines, a pocket and tunnel grafts within an aortic stent component of the invention.
FIG. 3A is a side view of another embodiment of a stent graft of the invention, wherein the proximal end of a proximal tunnel graft and a distal end of a distal tunnel graft of the embodiment are flared.

FIG. 2A is a side view of another embodiment of the invention. Therein, stent graft 36 is like that of FIG. 1, but, as shown, is rotated 90° about major longitudinal axis (18) and lacks distal bare stent (30). FIG. 2B is a side view of the embodiment of the invention shown in FIG. 2A and shows components of the invention in outline (dashed-lines) that are within the lumen defined by tubular aortic component (12). Specifically, stent graft (36) includes pocket (38) at fenestration (20). Pocket (38) defines pocket proximal opening (40) and pocket distal opening (42) opposite pocket proximal opening (40). Pocket proximal opening (40) of pocket (38) lies in plane A that is located proximally to proximal end (22) of fenestration (20). Pocket distal opening (42) lies in plane B located distally from distal end (24) of fenestration (20). As also shown in FIG. 2B, fenestration proximal end (22) lies in plane C, and fenestration distal end (24) lies in a plane D. Both plane C and plane D are essentially orthogonal to major longitudinal axis (18) of tubular aortic component (12). Plane A is parallel to and located proximal to plane C, and plane B is parallel to and lies distal to plane D.

Proximal tunnel graft (44) of stent graft (36) has proximal tunnel graft proximal end (46), proximal tunnel graft distal end (48) and proximal tunnel graft lumen (50). Proximal tunnel graft (44) extends proximally within the lumen of tubular aortic component (12) from pocket proximal opening (40) and is secured to proximal opening (40). Stent graft (36) also includes distal tunnel graft (52) having distal tunnel graft proximal end (54), distal tunnel graft distal end (56) and distal tunnel graft lumen (58). Distal tunnel graft (52) extends distally within the lumen of tubular aortic component (12) from pocket distal opening (42) and is secured to distal pocket opening (42).

At least one of proximal tunnel graft (44) and distal tunnel graft (52) is secured to an interior of tubular aorta component (12) by a suitable technique, such as is known to one skilled in the art, such as by a suture or biocompatible adhesive. For example, in one embodiment, proximal end (46) of proximal tunnel graft (44) is fixed to tubular aortic component (12) by proximal suture (60), and distal end (56) of distal tunnel graft (52) is fixed to tubular aortic component (12) by distal suture (61). Alternatively, at least one of proximal tunnel graft (44) and distal tunnel graft (52) can be attached to tubular aortic component (12) by more than a single suture, such as along an intermittent or continuous length (not shown), over a portion or the entire length of proximal tunnel graft (44) and distal tunnel graft (52), respectively.

Figure 3B:
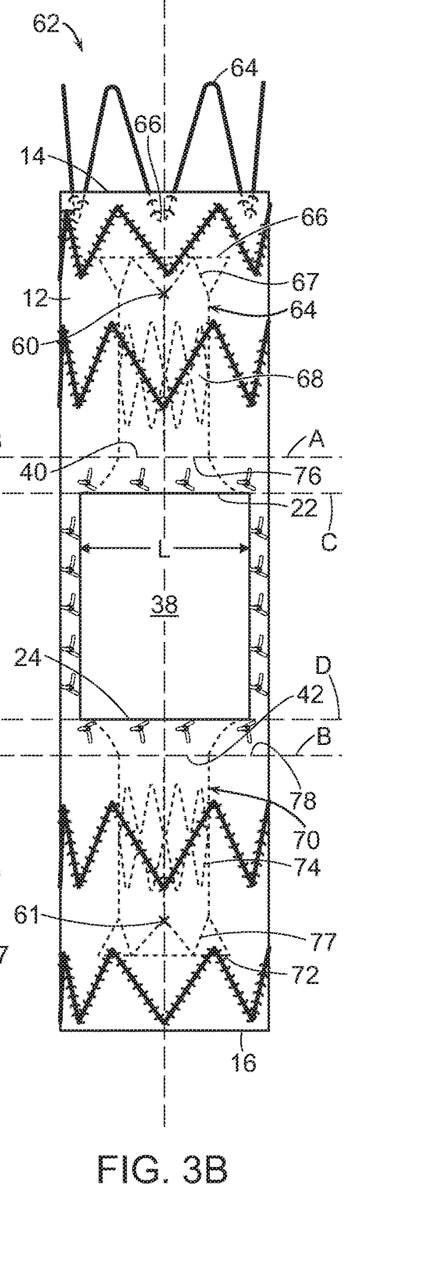
FIG. 3B is a side view of the embodiment of FIG. 3A rotated 90° about a major axis of the stent graft of the invention.

FIG. 3A is a side view of another embodiment of a stent graft of the invention. As shown therein, stent graft (62) is like that of FIGS. 2A and 2B, except that stent graft (62) includes proximal tunnel graft (64) having proximal tunnel graft proximal end (66) that is flared. Proximal tunnel graft (64) includes proximal tunnel graft stents (68) and stent graft (62) also includes distal tunnel graft (70) having distal tunnel graft distal end (56) that is flared. FIG. 3B is a side view of tunnel graft (62) but rotated 90° about axis (18). At least one stent (67, 77), supports the flared opening of at least one of proximal end (66) and distal end (72), respectively. Flared proximal tunnel graft proximal end opening (66) of proximal tunnel graft (64) and flared distal tunnel graft distal end opening (72) of distal tunnel graft (70), respectively, provides guidance to the surgeon during placement of a branch stent graft into a respective tunnel graft. In one embodiment, at least one of fenestration proximal end (22) and fenestration distal end (24) of fenestration (20) lies in plane C, D, respectively, orthogonal to major longitudinal axis (18) and has a length, L, shown in FIG. 3B. Length L is greater than the diameter of distal end (76) of the at least one proximal tunnel graft (64) or proximal end (78) of distal tunnel graft (70) extending from the respective proximal opening (40) and distal opening (42) of pocket (38).

Figure 4A:
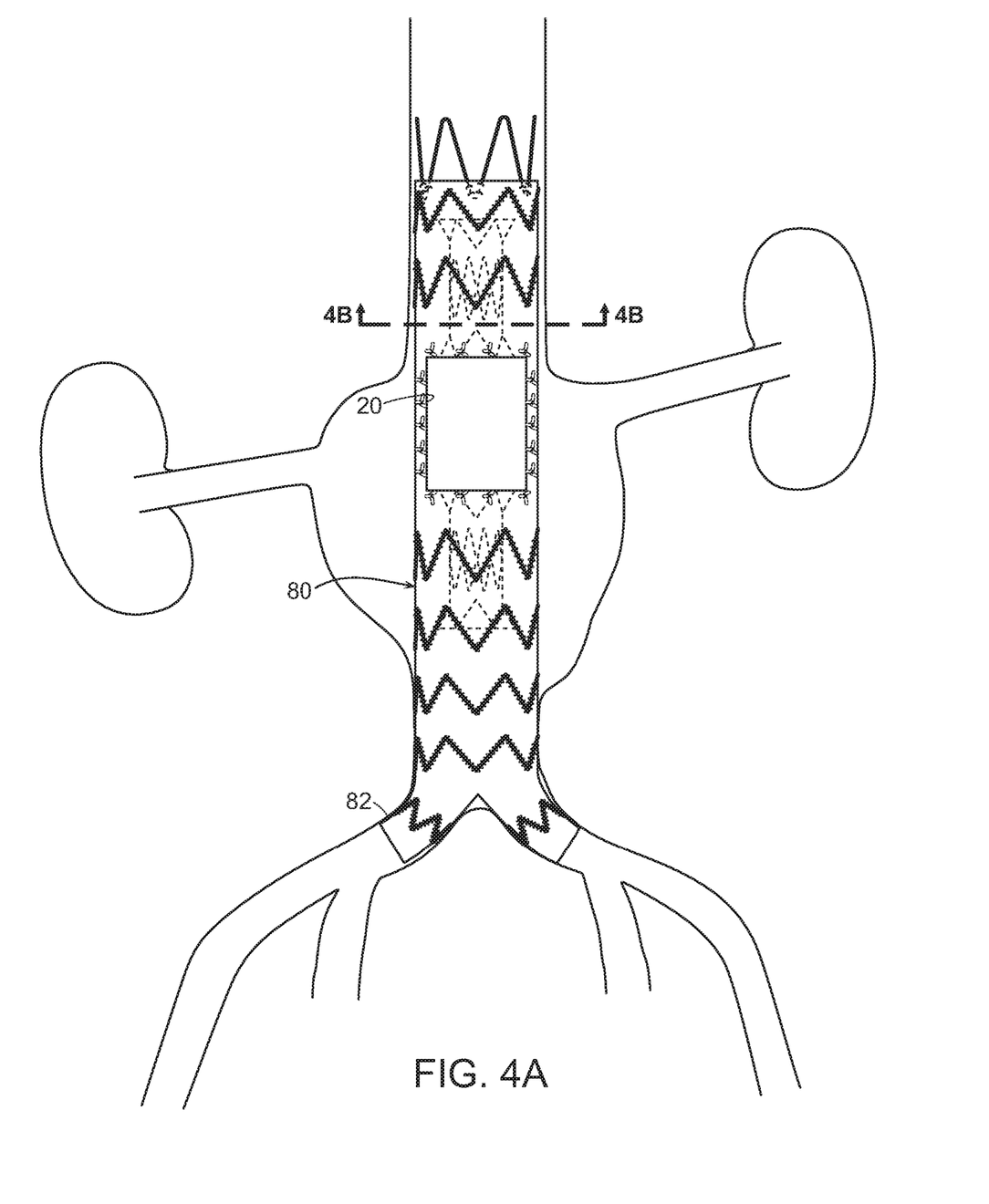
FIG. 4A is a side view of yet another embodiment of a stent graft of the invention after implantation at an aneurysm site in a subject, wherein the distal end of the aortic graft component is bifurcated.
Figure 4B:
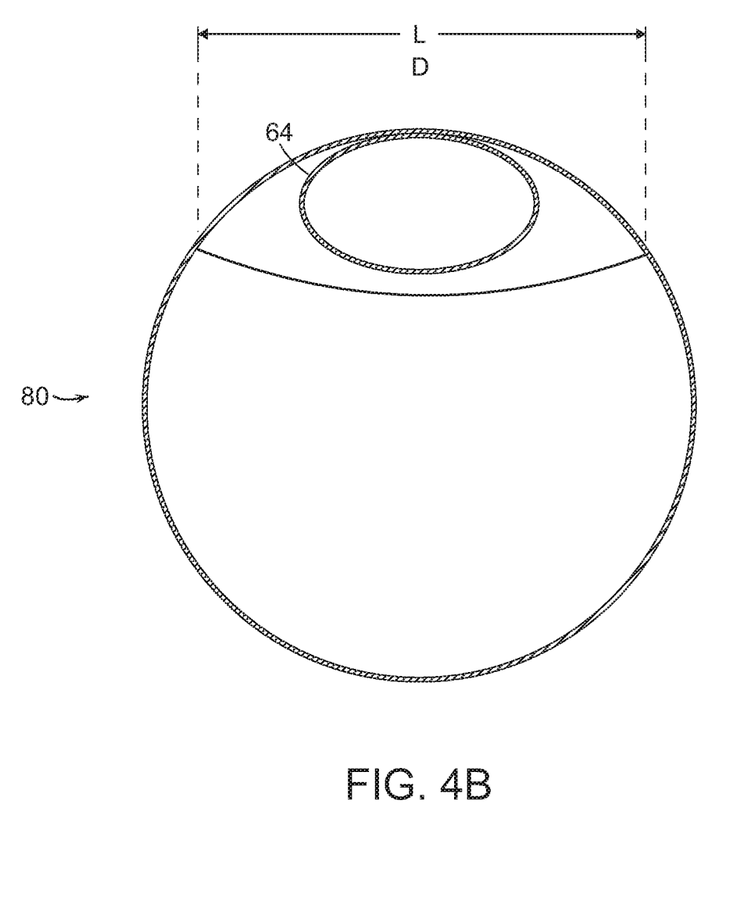
FIG. 4B is a cross-sectional view of the embodiment of the stent graft of the invention shown in FIG. 4A taken along line 4B-4B therein, and showing an end view of the proximal tunnel graft of FIG. 4A.
Figure 5:
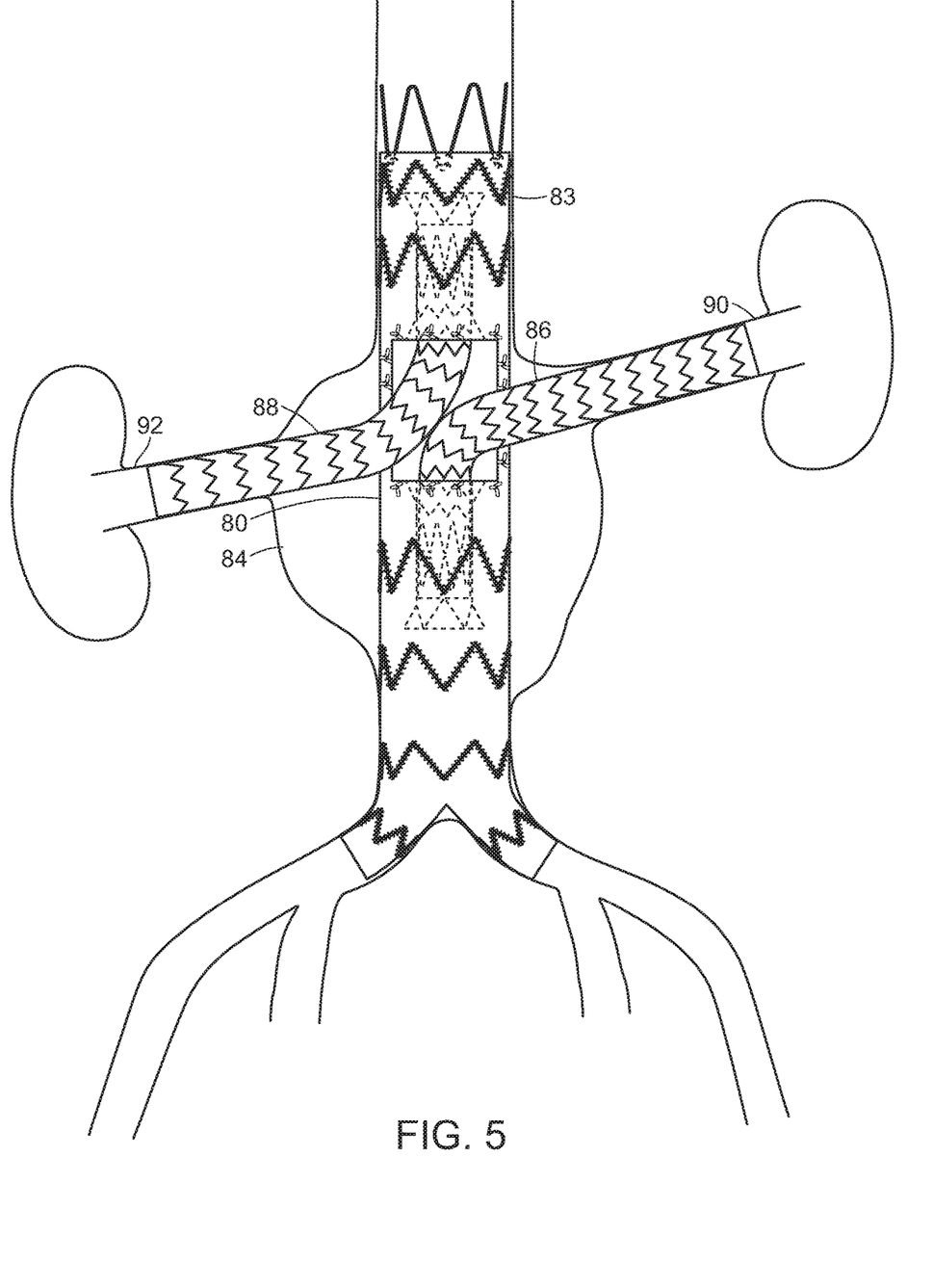
FIG. 5 is a side view of the stent graft of the invention of FIGS. 4A and 4B, and further including two branch stent grafts extending from the fenestration of the tubular aortic component of the invention after implantation at an aneurysm site in a subject.

FIG. 4A is a side view of another embodiment of a stent graft of the invention. Stent graft (80) is like that of stent graft (62) in FIGS. 3A and 3B, but includes bifurcated distal end (82). FIG. 4B is a cross-sectional view of stent graft 80 taken along line 4B-4B, of FIG. 4A. As shown in FIG. 4B, length L of the diameter of fenestration (20) is greater than that of diameter D of proximal tunnel graft (64) at proximal tunnel graft distal end (48). As shown in FIG. 5, stent graft (80) is implanted in abdominal aortic aneurysm (84) of a subject, and further includes branch stent grafts (86, 88), each implanted in a renal artery (90, 92), respectively.

Figure 6A:
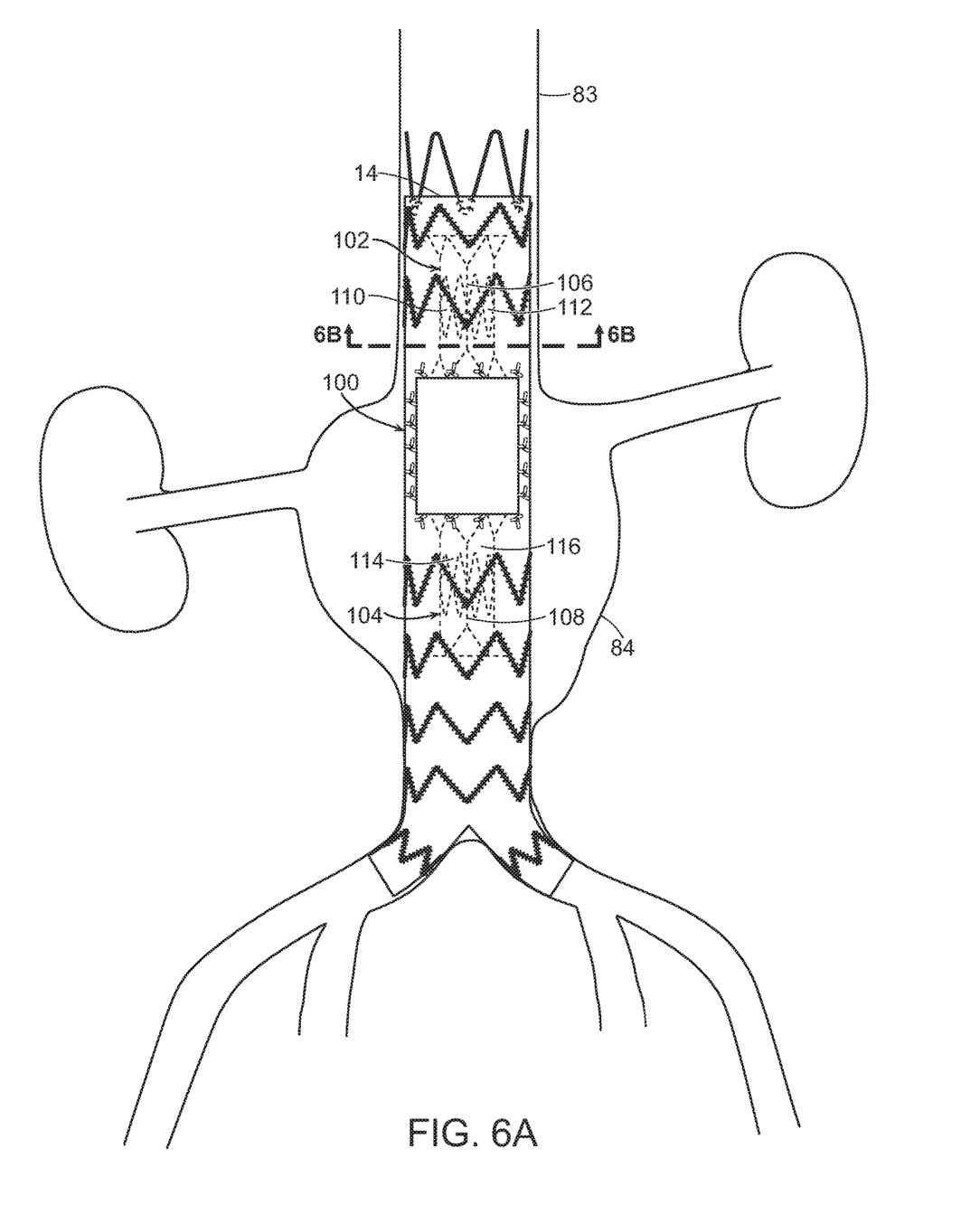
FIG. 6A is a side view of another embodiment of a stent graft of the invention, having a bifurcated distal end, and wherein the proximal and distal tunnel grafts are partitioned into sublumens, as shown after implantation at an aneurysm site in a subject.
Figure 6B:
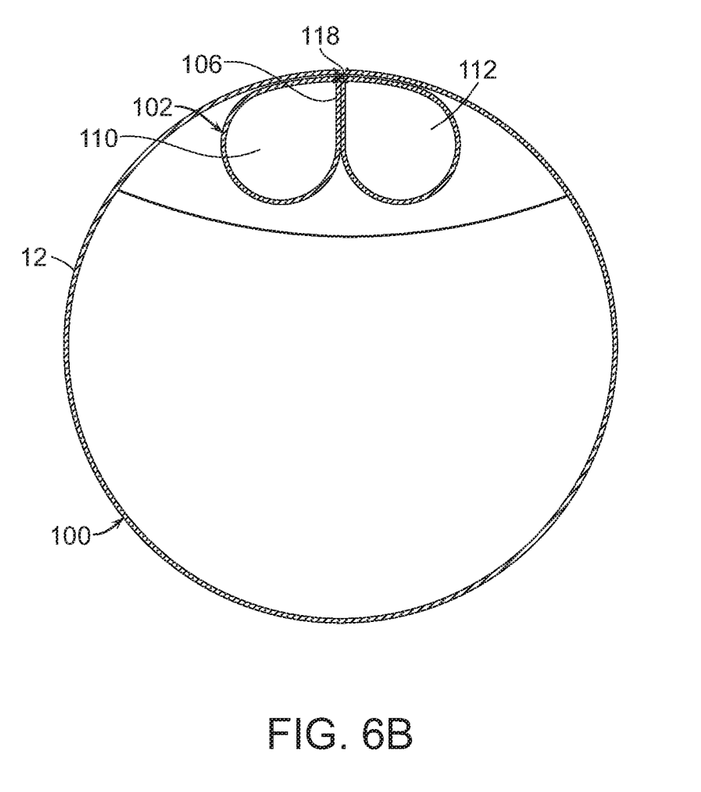
FIG. 6B is a cross sectional view of the embodiment of the stent graft of the invention shown in FIG. 6A taken along line 6B-6B therein, and showing an end view of the sublumens of proximal tunnel graft of FIG. 6A.

FIG. 6A is a side view of yet another embodiment of the stent graft of the invention. As shown therein, stent graft (100) is like stent graft (80) of FIGS. 4A, 4B and 5, but includes partitioned proximal tunnel graft (102) and partitioned distal tunnel graft (104). It is to be understood, however, that alternative embodiments are also possible, wherein only one or the other of proximal tunnel graft (102) or distal tunnel graft (104) is bifurcated. Septums (106, 108) partition each of the respective proximal and distal tunnel graft lumens (102, 104) into two proximal sublumens (110, 112) and distal sublumens (114, 116). Septums (106, 108) partition each of the respective proximal and distal tunnel graft lumens (102, 104) into two sublumens, to a point proximal or distal to openings of the respective tunnel graft lumens. Each sublumen has a sublumen proximal end and sublumen distal end, respectively. As shown in FIG. 6B, which is a cross-sectional view of stent graft 100 taken along line 6B-6B, proximal tunnel graft septum (106) can be formed by, for example, stitching proximal tunnel graft (102) along a center line to tubular aortic graft component (12) by stitching (118). It is to be understood that other methods of forming sublumens, such as are known in the art, can be employed in the alternative. For example, two parallel proximal or distal tunnel grafts can be employed instead of proximal and distal tunnel grafts that are stitched along a centerline to subdivide the lumens of each of them into sublumens.

Figure 7:
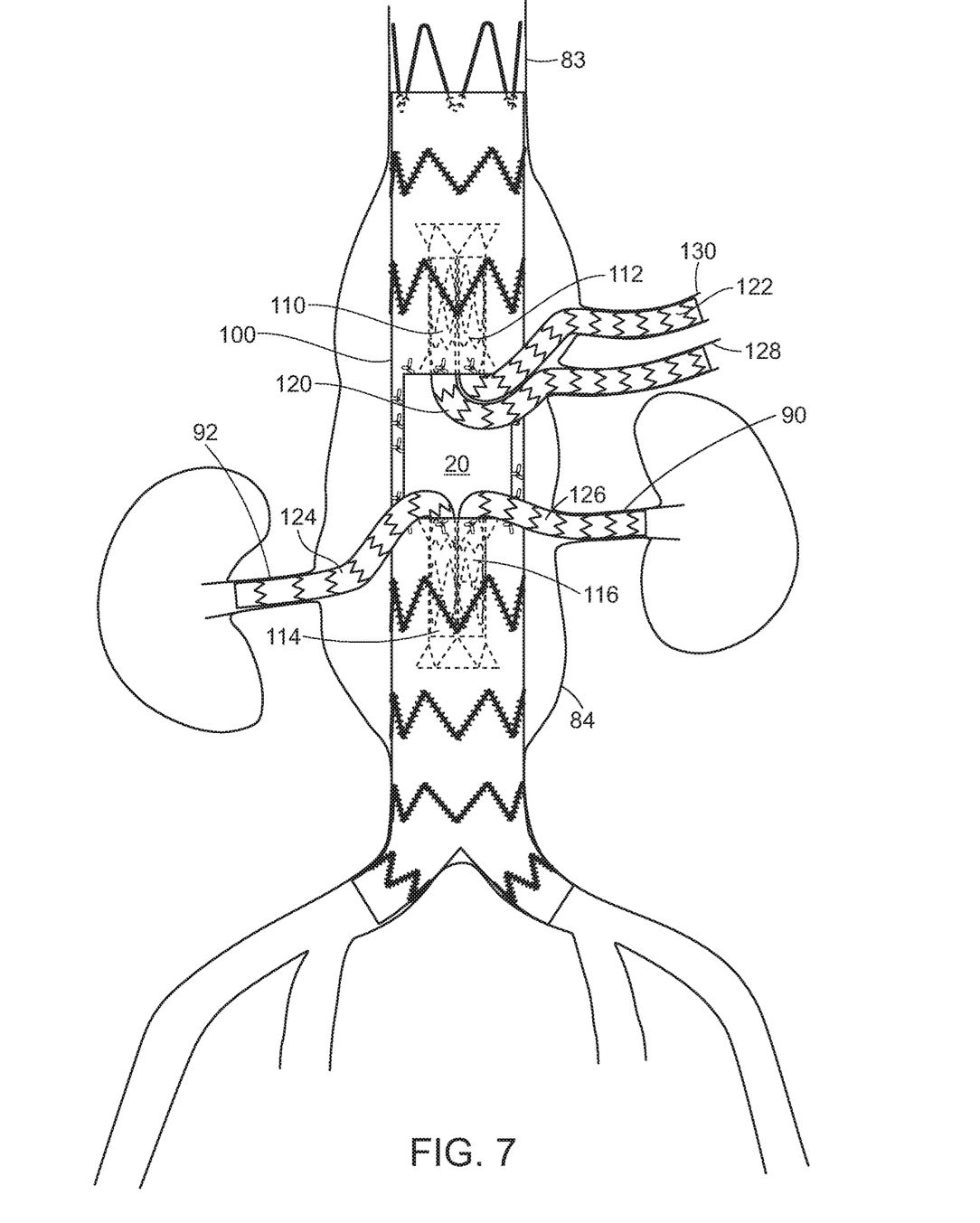
FIG. 7 is a side view of the stent graft of the invention of FIGS. 6A and 6B, and further including four branch stent grafts extending from a fenestration of a tubular aortic component of the invention after implantation at an aneurysm site of a subject.

As can be seen in FIG. 7 branch stent grafts (120, 122, 124, 126) extend through fenestration (20) and within at sublumens (110, 112, 114 and 116), respectively. Branch stent grafts (120, 122, 124, 126) extend from fenestration into renal arteries (90, 92), celiac artery (130), and superior mesenteric artery (128), respectively.

In another embodiment, the invention is a method for treating a suprarenal or thoracoabdominal aortic aneurysm. For example, with reference to FIGS. 6A, 6B and 7, stent graft is delivered through a femoral artery to aortic aneurysm site (84) of subject by radially and releasably constraining stent graft at the distal end of a control catheter of a delivery device (not shown). The fenestration of the stent graft is aligned at aneurysm site (84) with at least one branch artery (90, 92, 128, 130) at the aneurysm site (84), and then the stent graft is released from the delivery device and the delivery device is removed from the subject. Each of at least one branch stent graft is releasably constrained by a branch delivery device. Each branch stent graft (120, 122, 124, 126) is delivered by a respective branch delivery device through a lumen of a tunnel graft of the stent graft and then through fenestration (20) to aneurysm site (84). Branch stent grafts (120, 122, 124, 126) extending from fenestration (20) are directed by the respective branch delivery device into a branch of the aorta at aneurysm site (84), and secured in a respective proximal or distal tunnel graft lumen at one end and within the branch artery at the opposite end. Each branch stent graft is then released from the respective delivery device, which is then removed, thereby completing implantation and treating the suprarenal or thoracoabdominal aortic aneurysm.

Vascular repair devices of the invention can be implanted, for example, by transfemoral access. Additional vascular repair devices that are directed into the vascular repair devices of the invention can be implanted, for example, by supraaortic vessel access (e.g., through the brachial artery), or by transfemoral access or access from some other branch or branches of major blood vessels, including peripheral blood vessels.

The relevant teachings of all patents, published applications and references cited herein are incorporated by reference in their entirety. The relevant teachings of U.S. Pat. Nos. 8,292,943; 7,763,063; 8,308,790; 8,070,790; 8,740,963; 8,007,605; 9,320,631; 8,062,349; 9,198,786; 8,062,345; 9,561,124; 9,173,755; 8,449,595; 8,636,788; 9,333,104; 9,408,734; 9,408,735; 8,500,792; 9,220,617; 9,364,314; 9,101,506; 8,998,970; 9,554,929; 9,439,751; 9,592,112 and 9,655,712; U.S. patent application Ser. Nos. 14/226,005; 14/575,673; 15/166,818; 15/167,055; 14/272,818; 14/861,479; 15/478,424; 15/478,737 and PCT/US2017/025849 are also incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A stent graft (10), comprising:
a) a tubular aortic component (12) defining a lumen having a proximal end (14), a distal end (16), a major longitudinal axis (18), and defining a fenestration (20) between the proximal end (14) and the distal end (16), wherein the fenestration defines at least one of a fenestration proximal end (22) and a fenestration distal end (24) that lies in a plane orthogonal to the major longitudinal axis (18) of the tubular aortic component (12);
b) a pocket (38) at the fenestration, the pocket defining a pocket proximal opening (40) and a pocket distal opening (42) opposite the pocket proximal opening (40) within the lumen;
c) at least one proximal tunnel graft (44) having a proximal tunnel graft proximal end (46) and a proximal tunnel graft distal end (48), and defining at least one proximal tunnel graft lumen (50), the proximal tunnel graft extending proximally within the lumen from the proximal opening of the pocket, and being secured at its proximal end to the tubular aortic component (12); and
d) at least one distal tunnel graft (52) having a distal tunnel graft proximal end (54) and a distal tunnel graft distal end (56), and defining at least one distal tunnel graft lumen (58), the distal tunnel graft extending distally within the lumen from the distal opening of the pocket, and being secured at its distal end to the tubular aortic component (12), wherein the proximal end of the at least one proximal tunnel graft and the distal end of at least one of the at least one distal tunnel graft defines a flared opening, and wherein at least one of the fenestration proximal end (22) and the fenestration distal end (24) of the fenestration (20) lying in the plane orthogonal to the major longitudinal axis has a length greater than that of at least one of the total diameter of the distal end of the at least one proximal tunnel graft (44) and the total diameter of the proximal end of the at least one distal tunnel graft (52).

2. The stent graft of claim 1, wherein the distal end of the tubular aortic component (12) is bifurcated (82), thereby defining two legs of the stent graft.

3. The stent graft of claim 1, wherein the fenestration (20) defines a fenestration proximal end (22) that lies in a plane orthogonal to the major longitudinal axis (18) of the tubular aortic component (12).

4. The stent graft of claim 1, wherein the fenestration (20) defines a fenestration distal end (24) that lies in a plane orthogonal to the major longitudinal axis (18) of the tubular aortic component (12).

5. The stent graft of claim 1, further including at least one stent (67, 77) supporting the flared opening of at least one of the proximal tunnel graft proximal end (46) and the distal tunnel graft distal end (56).

6. The stent graft of claim 1, wherein the proximal tunnel graft proximal end (66) defines a flared opening (67).

7. The stent graft of claim 6, wherein the distal tunnel graft distal end (72) defines a flared opening.

8. The stent graft of claim 7, further including at least one stent supporting the distal tunnel graft (70) and the proximal tunnel graft (64).

9. The stent graft of claim 5, wherein both the distal tunnel graft distal end (72) and the proximal tunnel graft proximal end (66) define, respectively, a flared opening.

10. The stent graft of claim 1, further including a bare stent (28) having proximal apices and distal apices, the bare stent (28) affixed to the proximal end (14) of the tubular aortic component (12) at the distal apices and wherein the proximal apices extend proximally beyond the proximal end (14) of the tubular aortic component (12).

11. The stent graft of claim 1, further including at least two branch stent grafts, each branch stent graft extending through the fenestration (20) and within at least one of the proximal tunnel graft lumen and the distal tunnel graft lumen.

12. The stent graft of claim 11, further including at least two branch stent grafts, wherein the at least two branch stent grafts each extend through the fenestration, and wherein at least one of the branch stent grafts extends through one of the proximal tunnel graft lumen and the distal tunnel graft lumen.

13. The stent graft of claim 1, wherein at least one of the proximal tunnel graft and the distal tunnel graft includes a septum (106, 108) that partitions at least one of the proximal tunnel graft lumen and the distal tunnel graft lumen into two sublumens, each sublumen having a proximal end and a distal end.

14. The stent graft of claim 13, including a plurality of septums, wherein one septum partitions the proximal tunnel graft lumen into two lumens and one septum partitions the distal tunnel graft lumen into two sublumens.

15. The stent graft of claim 13, further including at least two branch stent grafts, each branch stent graft extending through the fenestration and within one of the two sublumens of the proximal tunnel graft.

16. The stent graft of claim 13, further including at least two branch stent grafts, each extending through the fenestration and each, independently, extending within one of the sublumens of the distal tunnel graft.

17. The stent graft of claim 13, wherein both of the proximal tunnel graft and the distal tunnel graft is supported by a stent graft.

18. The stent graft of claim 17, wherein each septum partitions the proximal and distal tunnel graft lumens into two sublumens to a point proximal to the flared distal opening of the distal tunnel graft or distal to the flared proximal opening of the proximal tunnel graft lumen.

19. The stent graft of claim 17, further including four branch stent grafts, all of which extend through the fenestration, and each of which extends independently within one of the sublumens.

\* \* \* \* \*